United States Patent

Marr-Leisy et al.

Patent Number: 5,516,509
Date of Patent: May 14, 1996

[54] QUICK-DRYING NAIL COATING FOR USE OVER NAIL POLISH

[75] Inventors: Debra Marr-Leisy, Long Beach; Naranbhai N. Patel, Orange, both of Calif.

[73] Assignee: International Beauty Design, Inc., Gardena, Calif.

[21] Appl. No.: 326,180

[22] Filed: Oct. 17, 1994

Related U.S. Application Data

[63] Continuation-in-part of Ser. No. 40,836, Mar. 31, 1993, abandoned.

[51] Int. Cl.$^6$ ............................................. A61K 7/043
[52] U.S. Cl. ............................ 424/61; 522/42; 522/44; 522/46; 522/89; 522/140
[58] Field of Search ........................ 424/61; 522/42, 522/44, 46, 89, 140

[56] References Cited

U.S. PATENT DOCUMENTS

| | | | |
|---|---|---|---|
| 3,790,801 | 2/1974 | Coleman | 250/453 |
| 3,864,294 | 2/1975 | Busch, Jr. | 260/28.5 A |
| 3,928,113 | 12/1975 | Rosenberg | 156/344 |
| 4,057,657 | 11/1977 | Garnett et al. | 427/44 |
| 4,058,442 | 11/1977 | Lee, Jr. et al. | 204/159.12 |
| 4,135,526 | 1/1979 | Matranga et al. | 132/73 |
| 4,229,431 | 10/1980 | Lee, Jr. et al. | 424/61 |
| 4,495,175 | 1/1985 | Chavin et al. | 424/101 |
| 4,596,260 | 6/1986 | Giuliano | 132/88.5 |
| 4,626,428 | 12/1986 | Weisberg et al. | 132/73 |
| 4,682,612 | 7/1987 | Giuliano | 132/73 |
| 4,704,303 | 11/1987 | Cornell | 427/53.1 |
| 4,708,866 | 11/1987 | Turco et al. | 424/61 |
| 4,729,904 | 3/1988 | Berthet et al. | 424/487 |
| 4,762,703 | 8/1988 | Abrutyn | 424/61 |
| 4,871,534 | 10/1989 | Montgomery | 424/61 |
| 5,118,495 | 6/1992 | Nafziger et al. | 424/61 |
| 5,130,551 | 7/1992 | Nafziger et al. | 424/61 |

OTHER PUBLICATIONS

Barbara Ayash, The Professional Manicurist's Handbook, 1976.

*Primary Examiner*—Jyothsan Venkat
*Attorney, Agent, or Firm*—William W. Haefliger

[57] ABSTRACT

A clear, photocurable coating composition to be applied over wet nail polish on a nail for binding with the wet nail polish upon exposure to ultraviolet light, consisting of: between 5% and 50% by weight of a film-forming polymer selected from the group consisting of:

i) cellulose esters ii) acrylic polymers, between 2% and 15% by weight of a photoinitiator selected from the group consisting of:

i) benzophenone ii) alkylphenyl ketone, and iii) cyclohexylphenyl ketone;

and between 40% and 85% by weight of a photoreactive monomer selected from the group consisting of methacrylic acid esters.

16 Claims, 1 Drawing Sheet

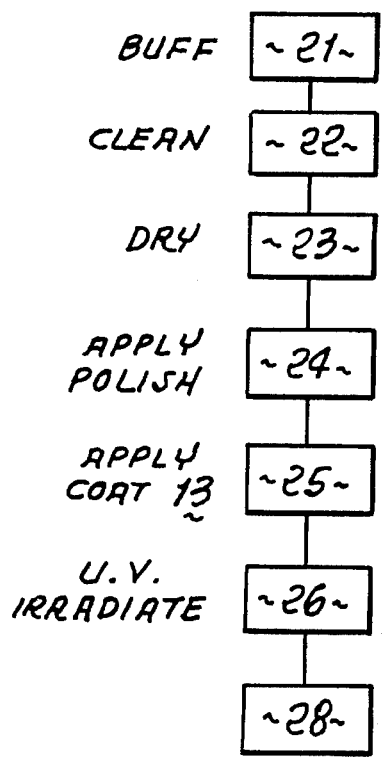
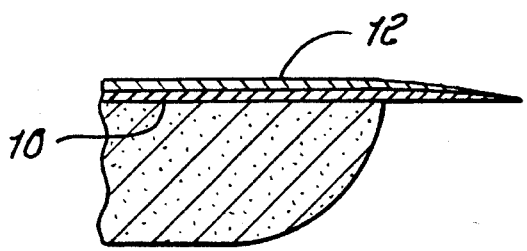
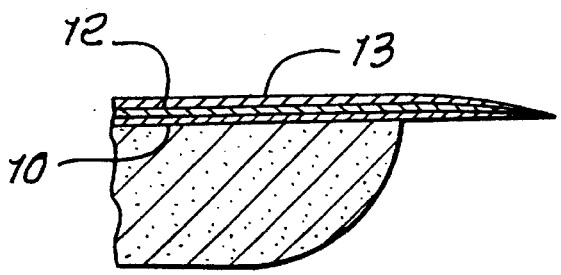
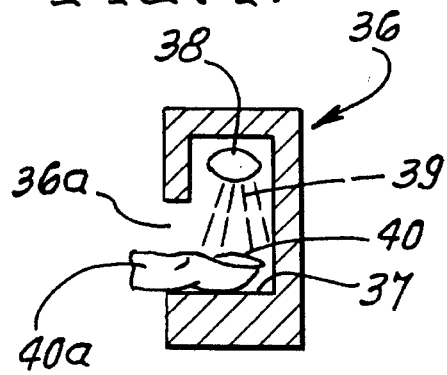

QUICK-DRYING NAIL COATING FOR USE OVER NAIL POLISH

This application is a continuation-in-part of Ser. No. 08/040,836 filed Mar. 31, 1993, now abandoned.

This invention relates generally to nail coating compositions applicable to nails, such as fingernails and toenails; and more particularly, it concerns a clear, photocurable, nail coating composition that is applied over wet nail polish (lacquer) of any color, and then hardened or is cured upon exposure to low-level, ultraviolet (UV) light, to protect and allow display of the polish.

There is need for a coating composition, as referred to, which, when applied over conventional wet nail polish, is then curable along with the wet polish, faster than curing of the polish itself. There is also need for such a coating which is durable and has better wear characteristics than the cured, unprotected polish itself; as well as need for such a coating which, when applied over wet polish and hardened, is insoluble in water.

A further need is for such a clear, protective coating which can be removed by application of conventional nail polish remover, whereby both the cured polish and the coating can be easily removed. Yet another need is for a coating composition, as referred to, which does not contain nitrocellulose. Nitrocellulose requires special handling because nitrocellulose is explosive. Although nitrocellulose itself is a powder, it cannot be shipped or handled in this form because of the potential for explosion; it must always be wetted by some solvent. For this reason, compositions containing nitrocellulose must always include some solvent. Nitrocellulose also yellows on exposure to light and heat, which makes it less desirable for a clear polish coating for cosmetic reasons.

U.S. Pat. No. 5,118,495 describes a UV curable nail coating that is applied over polish, and which hardens when exposed to UV light. That patent utilizes nitrocellulose as the base resin for the compositions. For the reasons given above, an improved composition would be achieved if film formers, other than nitrocellulose, could be utilized. Furthermore, it is desired that the composition exclude solvent, since it is desired to form a hard, protective surface over the polish on exposure to UV light, and the evaporation of solvents from the composition is a time dependent process.

SUMMARY OF THE INVENTION

It is a major object of the invention to provide a composition which meets one or more, or all, of the above-referred needs.

Another object is to provide a photoreactive nail coating composition that requires only low levels of ultraviolet radiation to polymerize the photoreactive component in the coating.

A further object is to provide a photoreactive nail coating composition that may be applied over multiple coats of nail polish (lacquer), and then dries to tack-free surface condition within only a few minutes of exposure to low-level, ultraviolet radiation.

Yet another object is to provide a photoreactive nail coating composition that is compatible with most commercially available nail polishes (lacquers).

Additional objects include the provision of a photoreactive nail coating composition which uses non-explosive ingredients, to simplify the manufacturing process; a composition which includes a non-yellowing, film-forming agent; a composition that allows the use of 100% UV reactive liquid components and that does not require use of solvent in the composition; and an improved composition that, after curing by ultraviolet light, can be removed using standard, commercially available nail polish remover.

While investigating compositions related to the present invention, it was discovered that ethyl methacrylate was far superior compared to other methacrylic acid esters, when used as the UV reactive liquid component in the composition. Further, it was surprisingly found that, when ethyl methacrylate was used as the liquid component, non-nitrocellulose polymers, such as cellulose esters and acrylic polymers, could be used as the film-forming component.

Basically, the composition of the invention, which meets the above needs, is applicable over wet nail polish on a nail, for binding with the wet nail polish upon exposure to low-level, ultraviolet light, and comprises:

a) between 5% and 50% by weight of a film-forming polymer selected from the group consisting essentially of:
  i) cellulose esters
  ii) acrylic polymers
b) between 2% and 15% by weight of a photoinitiator selected from the group consisting essentially of:
  i) benzophenone
  ii) alkylphenyl ketone
  iii) cyclohexylphenyl ketone
c) and between 40% and 85% by weight of a photoreactive monomer selected from the group consisting essentially of methacrylic acid esters, where the percentages by weight are based on the composition total weight.

Other ingredients may also be added to improve the handling or application of the coating. Examples are thickening agents, such as fumed silica, clay or pulverized glass, to modify viscosity; plasticizer, such as dibutyl phthalate, to increase flexibility of the cured coating; surfactants; slip agents; fragrance; etc.

The process of the invention includes applying the composition as a coating to a layer of wet nail polish (of conventional composition) on a nail; and then applying low-intensity, ultraviolet radiation to the coating and polish, to cure same. The hardened coating and polish may later be loosened, or removed, by application of commercially available nail polish remover. Such remover typically consists of solvents, such as acetone, ethyl alcohol, isopropyl alcohol, ethyl acetate, butyl acetate, or methylethyl ketone.

These and other objects and advantages of the invention, as well as the details of an illustrative embodiment, will be more fully understood from the following specification and drawings, in which:

DRAWING DESCRIPTION

FIG. 1 is a process flow diagram;

FIG. 2 is a vertical section taken through a fingernail onto which a wet polish layer or layers have been applied;

FIG. 3 is a view like FIG. 2 also showing further application of the clear, photocurable coating of the invention onto the polish layer or layers; and FIG. 4 is a vertical section showing ultraviolet radiation treatment of a coated fingernail, as in FIG. 3.

DETAILED DESCRIPTION

In FIG. 2, fingernail 10 is to undergo treatment. It is first prepared, as by standard practice used by nail technicians. For example, the nail is first buffed at 21 (in FIG. 1) to roughen its top surface. Next, it is cleaned at 22, as by application of a liquid solvent cleaner, preferably acetone, isopropyl alcohol, ethyl acetate, butyl acetate, or some combination of these.

After drying, as indicated at 23, a viscous, flowable, polish layer 12 is brushed, i.e., applied, as one or more layers upon the surface of nails 10, this step shown at 24. Layer 12 typically consists of conventional polish; and typical compositions include ethyl acetate, butyl acetate, isopropanol, toluene, and nitrocellulose.

Next, the composition of the invention is applied as a coating 13 onto the wet polish layer 12 (see step 25 in FIG. 2 and see FIG. 3), for binding with the wet nail polish upon exposure to ultraviolet light. That composition comprises:

a) between 5% and 50% by weight of a film-forming polymer selected from the group consisting essentially of:
  i) cellulose esters
  ii) acrylic polymers
b) between 2% and 15% by weight of a photoinitiator selected from the group consisting essentially of:
  i) benzophenone
  ii) alkylphenyl ketone
  iii) cyclohexylphenyl ketone
c) and between 40% and 85% by weight of a photoreactive monomer selected from the group consisting essentially of methacrylic acid esters, where the percentages by weight are based on the composition total weight.

The cellulose esters are selected from the group consisting essentially of cellulose acetate, cellulose acetate propionate, and cellulose acetate butyrate, with cellulose acetate butyrate being preferred. The acrylic polymers are selected from the group consisting essentially of polymers and copolymers of methacrylic acid esters, which include polymethylmethacrylate, polyethylmethacrylate, polybutylmethacrylate; and the methacrylic acid esters in the photoreactive monomer are selected from the group consisting essentially of ethyl methacrylate, cyclohexyl methacrylate, ethylhexyl methacrylate, butyl methacrylate, isobornyl methacrylate, and tetrahydrofurfuryl methacrylate, with ethyl methacrylate being preferred.

The layers 12 and 13 are then allowed to cure under ultraviolet radiation for a short time interval, i.e., between about 2–6 minutes, as indicated at 26, about three minutes being preferable.

FIG. 4 shows a fingernail 40, coated as described, inserted into a recess 36a in a receptacle 36, the finger 40a placed on a shelf 37 in the receptacle. An ultraviolet light bulb 38 at predetermined distance above the fingernail emits low level ultraviolet radiation 39 impinging on the nail. This treatment is continued to cure the coating to a hardened state. The resultant nail is presented at 28 in FIG. 1, in hardened state.

A typical ultraviolet bulb 38 is of 4 watt power, delivers between 0.15 and 0.75 milliwatts per square centimeter (preferably about 0.5 milliwatts per cm$^2$) at the location of the fingernail, and at 350 nanometers wavelength. Two such bulbs are typically employed.

Examples of the composition are as follows:

1. ethyl methacrylate—50% cellulose acetate butyrate—40% hydroxycyclohexyl phenyl ketone—10%
2. ethyl methacrylate—70% cellulose acetate butyrate—25% dimethoxyphenyl acetophenone—5%
3. ethyl methacrylate—72.5% cellulose acetate butyrate—25% dimethoxyphenyl acetophenone—2.5%
4. ethyl methacrylate—55% poly (methylmethacrylate/ ethyl methacrylate)—35% hydroxycyclohexyl phenyl ketone—10%
5. ethyl methacrylate—65% cellulose acetate butyrate—25% hydroxycyclohexyl phenyl ketone—10%
6. isobutyl methacrylate—10% ethyl methacrylate—63% cellulose acetate butyrate—22% dimethoxyphenyl acetophenone—5%
7. ethyl methacrylate—88% cellulose acetate butyrate—7% dimethoxyphenyl acetophenone—5%
8. ethyl methacrylate—68% cellulose acetate butyrate—22% dibutoxyethoxy ethyl adipate—5% dimethoxyphenyl acetophenone—5%
9. ethyl methacrylate—83% cellulose acetate butyrate—12% dimethoxyphenyl acetophenone—5%
10. ethyl methacrylate—72% cellulose acetate butyrate—18% dibutoxyethoxy ethyl adipate—5% dimethoxyphenyl acetophenone—5%
11. ethylmethacrylate—67.5% cellulose acetate butyrate—25% hydroxycyclohexyl phenyl ketone—5.0% dimethoxyphenyl acetophenone—2.5%
12. ethyl methacrylate—75% cellulose acetate butyrate—20% dimethoxyphenyl acetophenone—5%
13. ethyl methacrylate—76% cellulose acetate butyrate—17% dimethoxyphenyl acetophenone—5% dibutoxyethoxy ethyl adipate—2%
14. ethyl methacrylate—55% polyethyl methacrylate—35% dimethoxyphenyl acetophenone—10%
15. ethyl methacrylate—45% cellulose acetate butyrate—40% dimethoxyphenyl acetophenone—15%
16. ethyl methacrylate—70% cellulose acetate butyrate—20% dimethoxyphenyl acetophenone—10%

After formation of the protective, clear, hardened coating 13, as referred to, it, and layer 12, may easily be loosened and removed by application of standard, conventional nail polish remover, examples consisting of acetone, ethyl alcohol, isopropyl alcohol, ethyl acetate, butyl acetate, and methylethyl ketone.

We claim:

1. A clear, photocurable coating composition to be applied over wet nail polish on a nail for binding with said wet nail polish upon exposure to ultraviolet light, consisting of:

a) between 5% and 50% by weight of a film-forming polymer selected from the group consisting of:
  i) cellulose esters
  ii) acrylic polymers,
wherein said cellular esters are selected from the group consisting of:
  cellulose acetate
  cellulose acetate propionate, and
  cellulose acetate butyrate,
and wherein said acrylic polymers are selected from the group consisting of:
  polymethylmethacrylate,
  polyethylmethacrylate, and
  polybutylmethacrylate,
b) between 2% and 15% by weight of a photoinitiator selected from the group consisting of:
  i) benzophenone
  ii) alkylphenyl ketone, and
  iii) cyclohexylphenyl ketone,
c) and between 40% and 85% by weight of a photoreactive monomer selected from the group consisting of methacrylic acid esters, where said percentages by weight are based on the composition total weight, and wherein said methacrylic acid esters are selected from the group consisting of:
  ethyl methacrylate cyclohexyl methacrylate
ethylhexyl methacrylate
butyl methacrylate
isobornyl methacrylate, and
tetrahydrofurfuryl methacrylate.

2. The coating composition of claim 1 which consists of:
50% by weight of c) monomer which is ethyl methacrylate
40% by weight of a) polymer which is cellulose acetate butyrate
10% by weight of b) photoinitiator which is cyclohexylphenyl ketone.

3. The coating composition of claim 1 which consists of:
70% by weight of c) monomer which is ethyl methacrylate
25% by weight of a) polymer which is cellulose acetate butyrate
5% by weight of b) photoinitiator which is alkyl phenyl ketone.

4. The coating composition of claim 1 which consists of:
72.5% by weight of c) monomer which is ethyl methacrylate
25% by weight of a) polymer which is cellulose acetate butyrate
2.5% by weight of b) photoinitiator which is alkyl phenyl ketone.

5. The coating composition of claim 1 which consists of:
55% by weight of c) monomer which is ethyl methacrylate
35% by weight of a) polymer which is polymethylmethacrylate
10% by weight of b) photoinitiator which is cyclohexylphenyl ketone.

6. The coating composition of claim 1 which consists of:
65% by weight of c) monomer which is ethyl methacrylate
25% by weight of a) polymer which is cellulose acetate butyrate
10% by weight of b) photoinitiator which is cyclohexylphenyl ketone.

7. The coating composition of claim 1 which consists of:
85% c) monomer which is polyethylmethacrylate
7% by weight of a) polymer which is cellulose acetate butyrate
5% about by weight of b) photoinitiator which is alkyl phenyl ketone.

8. The coating composition of claim 1 which consists of:
83% by weight of c) monomer which is ethyl methacrylate
12% by weight of a) polymer which is cellulose acetate butyrate
5% by weight of b) photoinitiator which is alkyl phenyl ketone.

9. The coating composition of claim 1 which consists of:
75% by weight of c) monomer which is ethyl methacrylate
20% by weight of a) polymer which is cellulose acetate butyrate
5% by weight of b) photoinitiator which is alkyl phenyl ketone.

10. The coating composition of claim 1 which consists of:
55% by weight of c) monomer which is ethyl methacrylate
35% by weight of a) polymer which is polyethyl methacrylate
10% by weight of b) photoinitiator which is alkyl phenyl ketone.

11. The coating composition of claim 1 which consists of:
45% by weight of c) monomer which is ethyl methacrylate
40% by weight of a) polymer which is cellulose acetate butyrate
15% by weight of b) photoinitiator which is alkyl phenyl ketone.

12. The coating composition of claim 1 which consists of:
70% by weight of c) monomer which is ethyl methacrylate
20% by weight of a) polymer which is cellulose acetate butyrate
10% by weight of b) photoinitiator which is alkyl phenyl ketone.

13. A coating composition which consists of:
76% by weight of monomer which is ethyl methacrylate
17% by weight of polymer which is cellulose acetate butyrate
5% by weight of photoinitiator which is dimethoxyphenyl acetophenone
5% by weight of dibutoxyethoxy ethyl adipate.

14. A coating composition which consists of:
50% by weight of monomer which is ethyl methacrylate
40% by weight of polymer which is cellulose acetate butyrate
10% by weight of photoinitiator which is hydroxycyclohexyl phenyl ketone.

15. A coating composition which consists of:
70% by weight of monomer which is ethyl methacrylate
25% by weight of polymer which is cellulose acetate butyrate
5% by weight of photoinitiator which is dimethoxyphenyl acetophenone.

16. A coating composition which consists of one of the following:
a) 72.5% by weight of monomer which is ethyl methacrylate
25% by weight of polymer which is cellulose acetate butyrate
2.5% by weight of photoinitiator which is dimethoxyphenyl acetophenone,
b) 55% by weight of monomer which is ethyl methacrylate
35% by weight of polymer which is poly (methylmethacrylate/ethyl methacrylate)
10% by weight of photoinitiator which is hydroxycyclohexyl phenyl ketone,
c) 65% by weight of monomer which is ethyl methacrylate
25% by weight of polymer which is cellulose acetate butyrate
10% by weight of photoinitiator which is hydroxycyclohexyl phenyl ketone,
d) 10% by weight of isobutyl methacrylate
63% by weight of monomer which is ethyl methacrylate
22% by weight of polymer which is cellulose acetate butyrate
5% by weight of photoinitiator which is dimethoxyphenyl acetophenone, e) 88% by weight of monomer which is ethyl methacrylate 7% by weight of polymer which is cellulose acetate butyrate 5% by weight of photoinitiator which is dimethoxyphenyl acetophenone, f) 68% by weight of monomer which is ethyl methacrylate 22% by weight of polymer which is cellulose acetate butyrate 5% by weight of dibutoxyethoxy ethyl adipate 5% by weight of photoinitiator which is dimethoxyphenyl acetophenone, g) 83% by weight of monomer which is ethyl methacrylate 12% by weight of polymer which is cellulose acetate butyrate 5% by weight of photoinitiator which is dimethoxyphenyl acetophenone, h) 72% by weight of monomer which is ethyl methacrylate 18% by weight of polymer which is cellulose acetate butyrate 5% by weight of dibutoxyethoxy ethyl adipate 5% by weight of photoinitiator which is dimethoxyphenyl acetophenone, i) 67.5% by weight of monomer which is ethyl methacrylate 25% by weight of polymer which is cellulose acetate butyrate 5% by weight of hydroxycyclohexyl phenyl ketone 5% by weight of photoinitiator which is dimethoxyphenyl acetophenone, j) 75% by weight of monomer which is ethyl methacrylate 20% by weight of polymer which is cellulose acetate butyrate 5% by weight of photoinitiator which is dimethoxyphenyl acetophenone, k) 55% by weight of monomer which is ethyl methacrylate 35% by weight of polymer which is polyethyl methacrylate 10% by weight of photoinitiator which is dimethoxyphenyl acetophenone, l) 45% by weight of monomer which is ethyl methacrylate 40% by weight of polymer which is cellulose acetate butyrate 15% by weight of photoinitiator which is dimethoxyphenyl acetophenone, m) 70% by weight of monomer which is ethyl methacrylate 20% by weight of polymer which is cellulose acetate butyrate 10% by weight of photoinitiator which is dimethoxyphenyl acetophenone.

\* \* \* \* \*